United States Patent [19]  [11] 4,269,982
Nakai et al. [45] May 26, 1981

[54] PROCESS FOR PREPARING 5-AMINO-1,2,3-THIADIAZOLES

[75] Inventors: Mamoru Nakai; Katsumasa Harada; Yoshikatsu Mori, all of Ube, Japan

[73] Assignee: Ube Industries, Ltd., Ube, Japan

[21] Appl. No.: 142,718

[22] Filed: Apr. 22, 1980

[30] Foreign Application Priority Data
Dec. 27, 1979 [JP] Japan .................. 54/169292

[51] Int. Cl.³ .......................... C07D 285/06
[52] U.S. Cl. .................................. 548/127
[58] Field of Search .......................... 548/127

[56] References Cited

U.S. PATENT DOCUMENTS 4,113,733  9/1978  Kruger .................. 548/127

FOREIGN PATENT DOCUMENTS 2636994  2/1978  Fed. Rep. of Germany .......... 548/127

Primary Examiner—Alton D. Rollins
Attorney, Agent, or Firm—Frishauf, Holtz, Goodman & Woodward

[57] ABSTRACT

There is provided a process for preparing a 5-amino-1,2,3-thiadiazole represented by the formula $$\begin{array}{c} R-C-N \\ \parallel \quad \parallel \\ C \quad N \\ / \quad \backslash \; / \\ H_2N \quad S \end{array}$$

wherein R represents a hydrogen atom, a lower alkyl group or an aryl group, which comprises bringing a diazoacetonitrile represented by the formula $$\underset{R}{\overset{N_2CCN}{|}}$$

wherein R has the same meaning as defined above, into contact with hydrogen sulfide in the presence of a base or with a salt of hydrogen sulfide, in a solvent.

6 Claims, No Drawings

PROCESS FOR PREPARING 5-AMINO-1,2,3-THIADIAZOLES

This invention relates to a novel process for preparing 5-amino-1,2,3-thiadiazoles.

5-Amino-1,2,3-thiadiazoles have been utilized as raw materials for pharmaceuticals, agricultural chemicals and the like.

Conventionally, there have been proposed, as the methods for preparing 5-amino-1,2,3-thiadiazoles, a method in which chloroaldehyde ethoxycarbonylhydrazine is subjected to reaction with thionyl chloride followed by amination of the resulting reaction product (German Offenlegungsschrift No. P26 36 994); a method in which acetyl isothiocyanate is subjected to reaction with diazomethane [Chem. Ber. 99, 1618–31 (1966)]; and so on.

However, these conventional methods have problems in that the starting materials are expensive and tedious processes are required for preparing the starting materials, and hence are not necessarily advantageous from the economical standpoint.

As a result of extensive studies to establish an industrially advantageous process for preparing 5-amino-1,2,3-thiadiazoles, the present inventors have found that 5-amino-1,2,3-thiadiazoles can be prepared industrially by bringing a diazoacetonitrile into contact with hydrogen sulfide in the presence of a base or with a salt of hydrogen sulfide, in a solvent, and accomplished this invention.

The reaction according to this invention proceeds in accordance with the following equation.

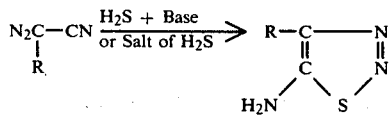

wherein R represents a hydrogen atom, a lower alkyl group or an aryl group.

The lower alkyl group represented by R in the above equation includes an alkyl group having 1 to 6 carbon atoms such as methyl, ethyl, propyl, butyl, pentyl and hexyl.

The aryl group represented by R in the above equation includes phenyl, p-tolyl, p-ethylphenyl and naphthyl.

The reaction can be carried out by a simple procedure, for example, by dissolving a diazoacetonitrile in a solvent and blowing hydrogen sulfide into the solution in the presence of a base or introducing a salt of hydrogen sulfide into the solution.

The diazoacetonitriles which are the starting materials in this invention are substances being difficult to be handled because of their exprosiveness or instability. However, these substances are entirely safe in such a solvent as ether, methylene chloride, etc.

The diazoacetonitriles can easily be prepared and obtained by subjecting an aminoacetonitrile to reaction with sodium nitrite, followed by extraction with ether, methylene chloride, etc. The solvents used herein are also suitable as the solvents for the reaction according to this invention. Accordingly, in the present invention, the thus obtained diazoacetonitrile are used in situ in a solution without being isolated so that there is no disadvantage such as dangerousness or difficulty in handling.

The aminoacetonitriles are precursors for glycine, which is commercially available in large amount, is inexpensive and can easily be available. Accordingly, the process according to this invention has also advantages in that the starting materials are less expensive and that the method for preparing the starting material is more simple as compared with the known processes.

As the solvent to be used in the present invention, any solvent can be useful as long as it is inert in the reaction and can dissolve the diazoacetonitrile. For example, there may be mentioned an aliphatic hydrocarbon such as n-hexane, n-heptane, etc.; an alicyclic hydrocarbon such as cyclohexane etc.; a halogenated hydrocarbon such as chloroform, methylene chloride, carbon tetrachloride, trichloroethylene, 1,2-dichloroethylene, 1,2-dichloroethane, etc.; an ether such as diethyl ether, dioxane, methyl cellosolve, ethyl cellosolve, etc.; an alcohol such as methanol, ethanol, etc; and water. These solvents may usually be used alone and may also be used in combination. Industrially however, there may advantageously be employed the solvent such a solvent as methylene chloride, ether, chloroform or n-hexane which are used for the extraction when a diazoacetonitrile is synthesized.

In cases where hydrogen sulfide is used, a base must be used in combination therewith.

As the base to be used in this invention, there may be employed either organic or inorganic bases.

As the organic bases, there may be mentioned, for example, methyl amine, ethyl amine, n-propyl amine, isopropyl amine, n-butyl amine, dimethyl amine, diethyl amine, trimethyl amine, triethyl amine, tributyl amine, allyl amine, α-ethoxyethyl amine, pyridine, ethylenediamine, hexamethylenediamine, hexamethyleneimine, hexamethylenetetramine, hydrazine, hydroxyl amine and the like.

As the inorganic bases, there may be mentioned for example, ammonia, an alcolate, or a hydroxide, a carbonate, an amide, etc., of an alkali metal or an alkaline earth metal. More specifically, there may be exemplified, bisides ammonia, sodium methoxide, sodium ethoxide, sodium hydroxide, potassium hydroxide, calcium hydroxide, potassium carbonate, sodium carbonate, calcium carbonate, sodium amide and the like. While the organic base generally is more advantageous as compared with the inorganic base, dimethyl amine, diethyl amine, trimethyl amine and triethyl amine are preferred in particular among the organic bases. The amount of the base to be employed is not less than 0.1 mole, preferably 0.5 to 5 moles, per one mole of the starting diazoacetonitrile.

In cases where hydrogen sulfide is used, hydrogen sulfide is blown into the system thus maintained over 0.1 to 2 hours so that the amount may be equimolar to that of the diazoacetonitrile.

In the present invention, 5-amino-1,2,3-thiadiazoles may also be obtained by contacting an acetonitrile with a salt between hydrogen sulfide and a base as mentioned above. As the salt of hydrogen sulfide, there may be mentioned either a sulfide or a hydrosulfide. As the preferred salts of hydrogen sulfide, there may be mentioned a salt between hydrogen sulfide and a base which may preferably be employed in combination with hydrogen sulfide in cases where hydrogen sulfide per se is used. Usually, the salt of hydrogen sulfide is employed in equimolar amount or more based on the diazoacetonitrile to be used.

The contact is carried out under ordinary pressure at a relatively low temperature, i.e., below 20° C. preferably at a temperature of −5° to 15° C., since the starting diazoacetonitrile is liable to be decomposed at a higher temperature.

After completion of the contact, the desired 5-amino-1,2,3-thiadiazole partially precipitates, which is collected by filtration. The resulting filtrate is concentrated to precipitate the remaining desired product from the mother liquor.

Next, Examples of the present invention will be illustrated below.

EXAMPLE 1

In a reactor was placed 300 g. of a solution of 0.07 mole of diazoacetonitrile in methylene chloride, and the mixture was maintained at around 3° C. and stirred. After 15 g. of triethyl amine was added dropwise thereto over 5 minutes, hydrogen sulfide gas was blown thereto over 30 minutes at a rate of 52 ml/min. Seven minutes after starting of the blowing of hydrogen sulfide gas, crystals of the desired product began to precipitate. After blowing of the hydrogen sulfide gas, the reaction mixture was stirred for 15 minutes and 3.2 g. of the precipitated product was collected by filtration. Subsequently, the filtrate was concentrated under reduced pressure at a temperature of below 10° C. to give 1.4 g. of crystals of the desired product.

EXAMPLES 2 to 10

Experiments were run in the same manner as in Example 1 except that the starting materials, solvents, bases and the used amounts thereof were changed to those as shown in the following Table. The results are shown in Table.

TABLE

| Example No. | Used starting material | Used solvent | Used base (g.) | Product (g.) |
|---|---|---|---|---|
| 1 | diazoacetonitrile | methylene chloride | triethyl amine (15 g.) | 5-amino-1,2,3-thiadiazole (4.6 g.) |
| 2 | diazoacetonitrile | methylene chloride | pyridine (11.2 g.) | 5-amino-1,2,3-thiadiazole (3.2 g.) |
| 3 | diazoacetonitrile | chloroform | n-butyl amine (10 g.) | 5-amino-1,2,3-thiadiazole (3.4 g.) |
| 4 | diazoacetonitrile | ethyl ether | diethyl amine (10 g.) | 5-amino-1,2,3-thiadiazole (1.5 g.) |
| 5 | diazoacetonitrile | methylene chloride | hexamethyleneimine (14 g.) | 5-amino-1,2,3-thiadiazole (3.9 g.) |
| 6 | diazoacetonitrile | trichloroethylene | 2-ethoxyethyl amine (12 g.) | 5-amino-1,2,3-thiadiazole (3.2 g.) |
| 7 | diazoacetonitrile | 1,2-dichloroethane | ethylenediamine (8 g.) | 5-amino-1,2,3-thiadiazole (2.7 g.) |
| 8 | diazoacetonitrile | methyl cellosolve | allyl amine (8 g.) | 5-amino-1,2,3-thiadiazole (2.8 g.) |
| 9 | ethyldiazoacetonitrile | methylene chloride | triethyl amine (15 g.) | 4-ethyl-5-amino-1,2,3-thiadiazole (6.8 g.) |
| 10 | phenyldiazoacetonitrile | methylene chloride | diethyl amine (10 g.) | 4-phenyl-5-amino-1,2,3-thiadiazole (8.9 g.) |

EXAMPLE 11

In a reactor were placed 200 g. of a solution of 0.077 mole of diazoacetonitrile in methylene chloride and 80 ml. of n-hexane, and the mixture was maintained at around 0° C. and stirred. After 15 g. of triethyl amine was added dropwise thereinto over 15 minutes, hydrogen sulfide gas was blown thereinto over 30 minutes at a rate of 52 ml/min., followed by filtration and concentration, giving 5.3 g of 5-amino-1,2,3-thiadiazole.

EXAMPLE 12

In a reactor were placed 200 g. of a solution of 0.083 mole of diazoacetonitrile in methylene chloride and 80 ml. of n-hexane, and the mixture was maintained at around 5° C. and stirred, followed by dropwise addition thereto of 7 g. of triethyl amine over 5 minutes. Subsequently, hydrogen sulfide gas was blown thereinto over 30 minutes at a rate of 28 ml/min., followed by filtration and concentration, giving 6.2 g. of 5-amino-1,2,3-thiadiazole.

EXAMPLE 13

In a reactor were placed 300 g. of a solution of 0.08 mole of diazoacetonitrile in methylene chloride and 9 g. of diethyl amine, and the mixture was maintained at around 3° C. and stirred. After hydrogen sulfide gas was blown thereinto over 45 minutes at a rate of 52 ml/min., followed by filtration and concentration, giving 4.5 g. of 5-amino-1,2,3-thiadiazole.

EXAMPLE 14

In a reactor was placed 200 ml. of a solution of 0.07 mole of diazoacetonitrile in ethanol, and the resulting solution was maintained at around −3° C. and stirred. To the stirred solution was added dropwise 100 ml. of a solution of 0.07 mole of anhydrous sodium hydrosulfide in ethanol over 30 minutes, followed by stirring at the same temperature for 15 minutes. As the result, 3.9 g. of 5-amino-1,2,3-thiadiazole was obtained.

EXAMPLE 15

In a reactor was placed 250 ml. of a solution of 0.07 mole of diazoacetonitrile in methyl alcohol, and the resulting solution was maintained at around −3° C. and stirred. To the stirred solution was added dropwise 20 ml. of a solution of 0.015 mole of sodium methoxide in methyl alcohol over 5 minutes. After hydrogen sulfide gas was blown thereinto over 30 minutes at a rate of 50 ml/min., the reaction mixture was further stirred at the same temperature for 15 minutes.

As the result, 2.9 g. of 5-amino-1,2,3-thiadiazole was obtained.

EXAMPLE 16

In a reactor was placed 100 ml. of a solution of 0.05 mole of diazoacetonitrile in methylene chloride, and the mixture was maintained at −7° C. and stirred. To the stirred solution was added dropwise 100 ml. of a 50%-ethanolic solution of 3.90 g. (0.05 mole) of anhydrous sodium sulfide ($Na_2S$) over 30 minutes, and then the resulting mixture was further stirred at the same temperature for 15 minutes. As the result, 2.4 g. of 5-amino-1,2,3-thiadiazole was obtained.

We claim:

1. A process for preparing a 5-amino-1,2,3-thiadiazole represented by the formula

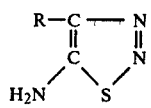

wherein R represents a hydrogen atom, a lower alkyl group or an aryl group, which comprises bringing a diazoacetonitrile represented by the formula

wherein R has the same meaning as defined above, into contact with hydrogen sulfide in the presence of a base or with a salt of hydrogen sulfide, in a solvent.

2. A process according to claim 1 wherein said solvent is methylene chloride, ether, chloroform or n-hexane.

3. A process according to claim 1 wherein said base is an amine series compound.

4. A process according to claim 3 wherein said amine series compound is dimethyl amine, diethyl amine, dibutyl amine, trimethyl amine, triethyl amine or tributyl amine.

5. A process according to claim 1 wherein said base is sodium hydroxide, potassium hydroxide, ammonia, sodium methoxide or sodium ethoxide.

6. A process according to claim 1 wherein said reaction is carried out at a temperature of −5° to 15° C.

* * * * *